US00PP33476P2

(12) United States Plant Patent
Blaker et al.

(10) Patent No.: US PP33,476 P2
(45) Date of Patent: Sep. 14, 2021

(54) STRAWBERRY PLANT NAMED 'SANTA MARIA'

(50) Latin Name: *Fragaria ananassa*
Varietal Denomination: SANTA MARIA

(71) Applicant: STRAWBERRY SCIENCES, LLC, Watsonville, CA (US)

(72) Inventors: Kendra M. Blaker, Archer, FL (US); Michael D. Nelson, Watsonville, CA (US); Stephen M. Ackerman, Salinas, CA (US); Daniel S. Nelson, Watsonville, CA (US)

(73) Assignee: STRAWBERRY SCIENCES, LLC, Watsonville, CA (US)

( * ) Notice: Subject to any disclaimer, the term of this patent is extended or adjusted under 35 U.S.C. 154(b) by 0 days.

(21) Appl. No.: 15/931,558

(22) Filed: May 13, 2020

(51) Int. Cl.
*A01H 5/08* (2018.01)
*A01H 6/74* (2018.01)

(52) U.S. Cl.
USPC ..... Plt./208
CPC ..... *A01H 6/7409* (2018.05)

(58) Field of Classification Search
USPC ..... Plt./208, 209
CPC ..... A01H 5/0893
See application file for complete search history.

(56) References Cited

U.S. PATENT DOCUMENTS

PP20,363 P2 * 9/2009 Chandler ..... A01H 6/7409
Plt./208

* cited by examiner

*Primary Examiner* — Kent L Bell
(74) *Attorney, Agent, or Firm* — Foley & Lardner LLP

(57) ABSTRACT

This invention relates to a new and distinct variety of strawberry plant named 'SANTA MARIA'. This new strawberry plant named 'SANTA MARIA' is primarily adapted to the growing conditions of the West Central Florida, and is primarily characterized by its achenes typically set even to slightly below the surface of the fruit, good fruit flavor with firm flesh, moderately creased fruit, early time of first flower and fruit, medium plant size, and large fruit.

4 Drawing Sheets

Latin name of the genus and species of the plant claimed: *Fragaria ananassa.*

Variety denomination: 'SANTA MARIA'.

BACKGROUND

The present invention relates to a new and distinct strawberry variety named 'SANTA MARIA'. This new variety is a result of a controlled cross made in 2012 in an ongoing breeding program between strawberry variety designated 'Red Merlin' (Protected; Israel PBR Grant No. 2906) as the seed (female) parent, and the unreleased, unpatented strawberry breeding selection designated 'BG-5.321' as the pollen (male) parent. The variety is botanically known as *Fragaria ananassa.*

The seedling resulting from the aforementioned cross was selected from a controlled breeding plot in Hillsborough County, Fla. in the fall/winter of 2013-2014. After its selection, the new variety was asexually propagated by stolons in both Siskiyou County, Calif. and San Joaquin County, Calif. The new variety was extensively tested over the next several years in fruiting fields in Hillsborough County, Fla. This propagation has demonstrated that the combination of traits disclosed herein as characterizing the new variety are fixed and remain true-to-type through successive generations of asexual reproduction.

SUMMARY

'SANTA MARIA' is primarily adapted to the climate and growing conditions of West Central Florida. The subtropical climate of West Central Florida provides the day length and moderate temperatures needed to produce a strong, vigorous plant and maintain fruit quality during the fall and winter production months.

The following traits have been repeatedly observed and are determined to be unique characteristics of 'SANTA MARIA', which in combination distinguish this strawberry plant as a new and distinct variety:

1. Achenes typically set even to slightly below the surface of the fruit;
2. Good fruit flavor with firm flesh;
3. Moderately creased fruit;
4. Early time of first flower and fruit;
5. Medium plant size; and
6. Large fruit size 'Florida Radiance' (U.S. Plant Pat. No. 20,363) has been a dominant strawberry variety in Hillsborough County, Fla. for more than ten years. The fruit of 'SANTA MARIA' are similar in flavor and firmness to 'Florida Radiance', but the fruits of 'SANTA MARIA' are greater in size, and more uniform and conical in shape during the early season. The achenes of 'Florida Radiance' are more sunken than those of 'SANTA MARIA'. In side-by-side comparisons from the 2017-2018 season (Nov. 11, 2017 to Feb. 23, 2018) and the 2018-2019 season (Nov. 15, 2018 to Feb. 27, 2019), 'SANTA MARIA' compares with 'Florida Radiance' (U.S. Plant Pat. No. 20,363) in the following combination of characteristics as described in Table 1.

TABLE 1

| Characteristic | 'SANTA MARIA' | 'Florida Radiance' (U.S. Plant Pat. No. 20,363) |
|---|---|---|
| 2017-2018 | | |
| November marketable yield (gm/plt) | 70.0 | 29.7 |
| December marketable yield (gm/plt) | 26.3 | 23.7 |
| January marketable yield (gm/plt) | 90.9 | 110.4 |
| February marketable yield (gm/plt) | 217.1 | 203.9 |
| Season marketable yield (grm/plt) | 404.3 | 367.7 |
| Season average berry size (gm) | 30.5 | 25.5 |
| Flavor | Good | Good |
| 2018-2019 | | |
| November marketable yield (gm/plt) | 61.0 | 27.0 |
| December marketable yield (gm/plt) | 36.7 | 23.8 |
| January marketable yield (gm/plt) | 59.5 | 49.7 |
| February marketable yield (gm/plt) | 212.4 | 394.5 |
| Season marketable yield (grm/plt) | 369.5 | 495.1 |
| Season average berry size (gm) | 32.6 | 34.5 |
| Flavor | Good | Good |

For identification, a series of molecular markers have been determined for this new variety.

'SANTA MARIA' differs from its parents, 'Red Merlin' and 'BG-5.321' by the following combination of characteristics as described in Tables 2 and 3.

TABLE 2

| Characteristic | 'SANTA MARIA' | 'Red Merlin' |
|---|---|---|
| Fruit: Size | Large | Medium |
| Fruit: Early marketable yield | High | Medium |
| Plant: Vigor | Medium to high | Medium |

TABLE 3

| Characteristic | 'SANTA MARIA' | 'BG-5.321' |
|---|---|---|
| Fruit: Size | Large | Very large |
| Fruit: Marketable yield | High | Very high |
| Fruit: Seed position | Even with surface | Moderately sunken |

BRIEF DESCRIPTION OF THE DRAWINGS

The accompanying color photographs illustrate the overall appearance of typical specimens of the new strawberry variety 'SANTA MARIA' at various stages of development, as true as it is reasonably possible with color reproductions of this type. Color in the photographs may differ slightly from the color value cited in the botanical descriptions which accurately describe the color of 'SANTA MARIA'. The depicted plant and plant parts of the new strawberry variety 'SANTA MARIA' are approximately five months old. The photographs were taken in Hillsborough County, Fla.

DETAILED BOTANICAL DESCRIPTION

Figure 1:
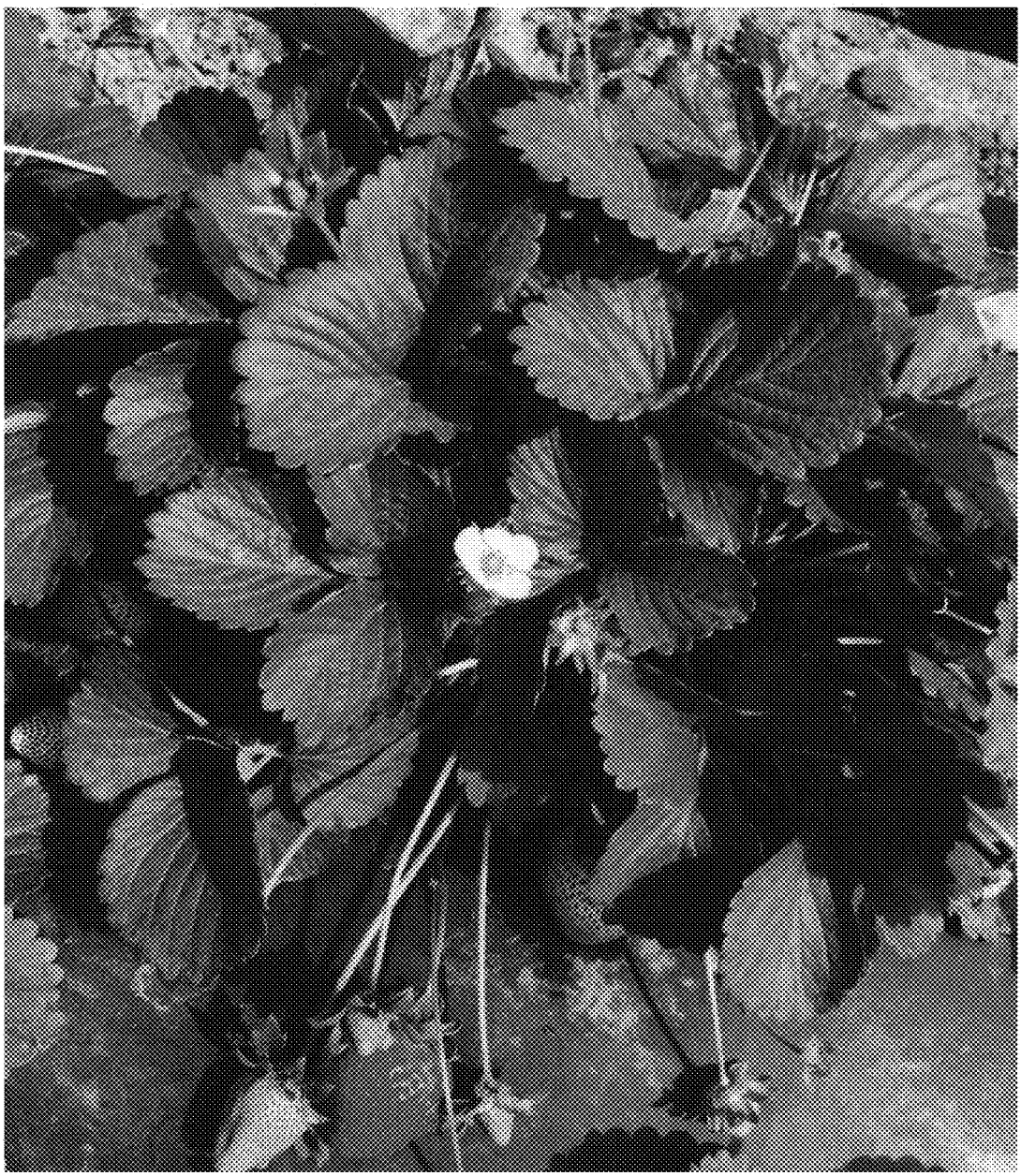
FIG. 1 shows typical fruiting field characteristics of 'SANTA MARIA', taken in the month of March 2020.
Figure 2:
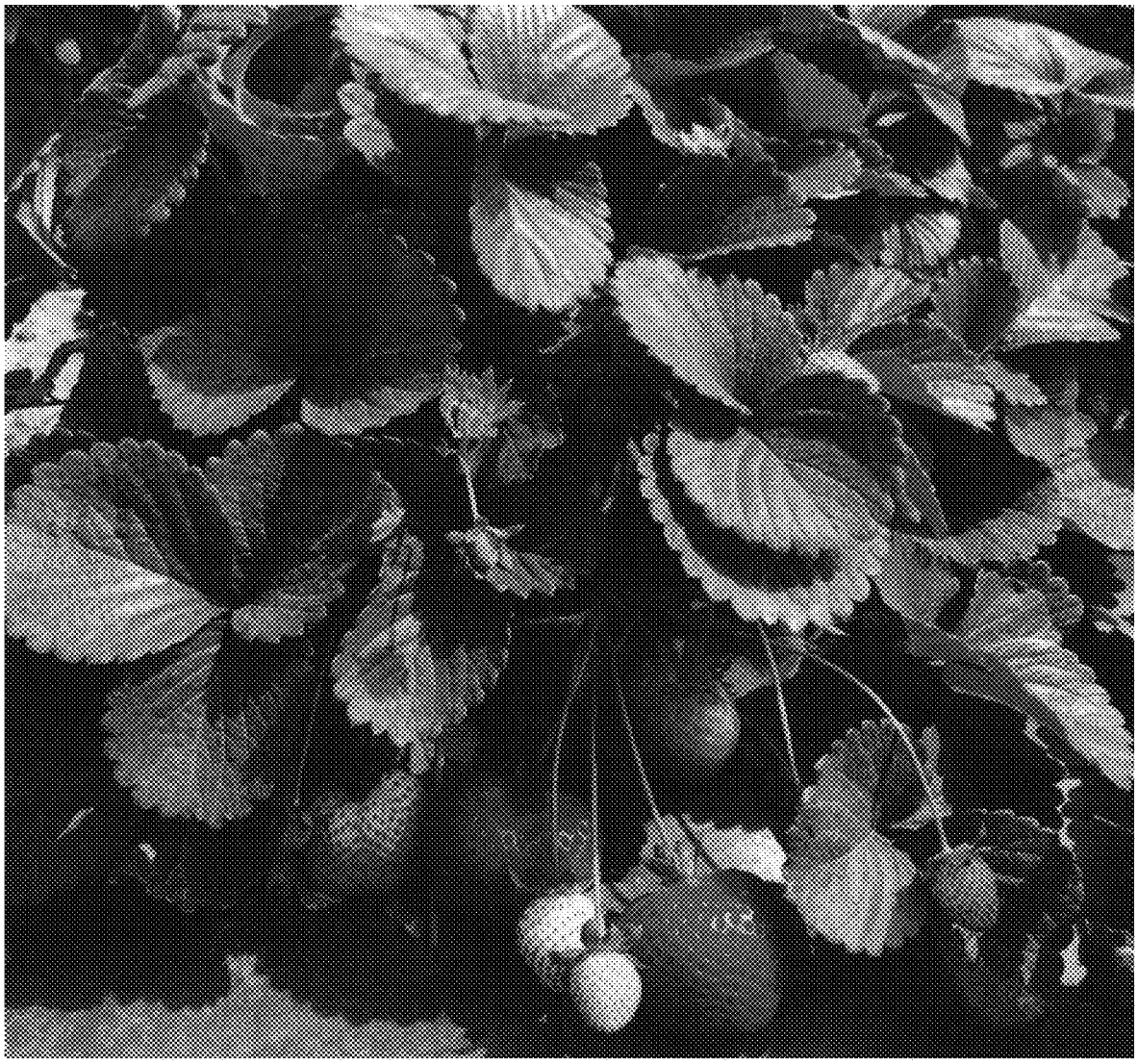
FIG. 2 shows a close-up view of a typical plant of 'SANTA MARIA', taken in the month of March 2020.
Figure 3:
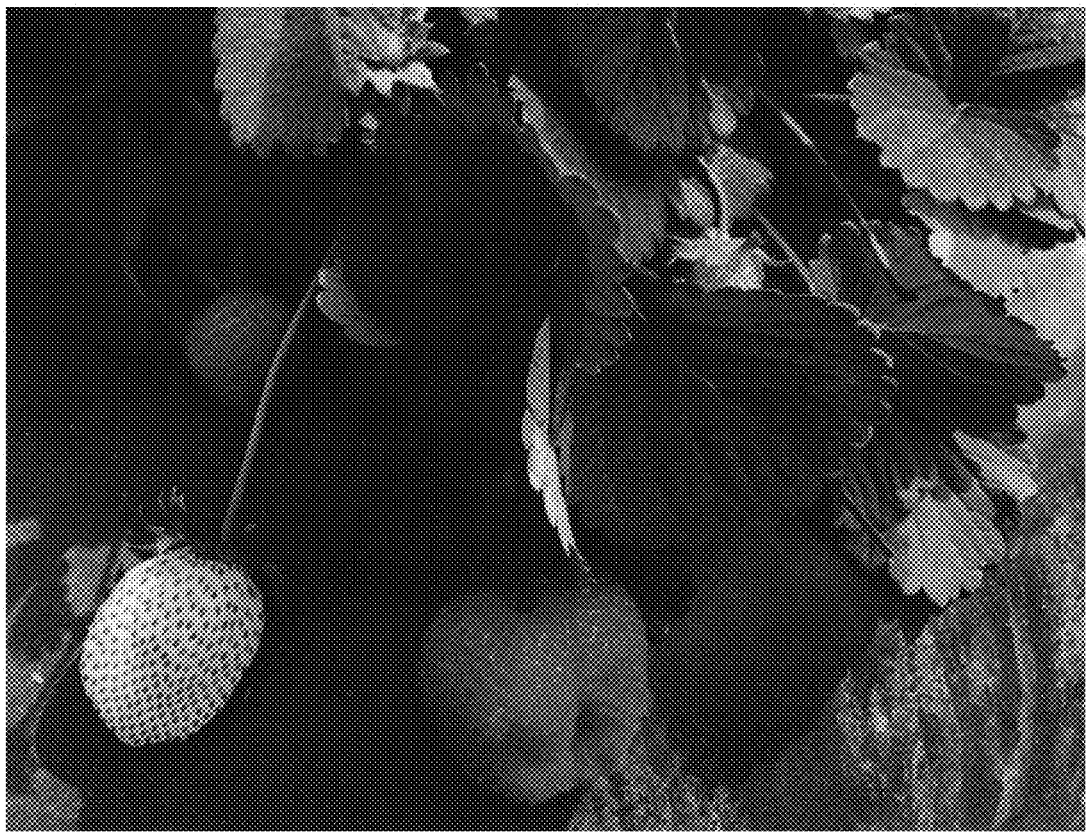
FIG. 3 shows typical mature and immature field fruit of 'SANTA MARIA', taken in the month of March 2020.
Figure 4:
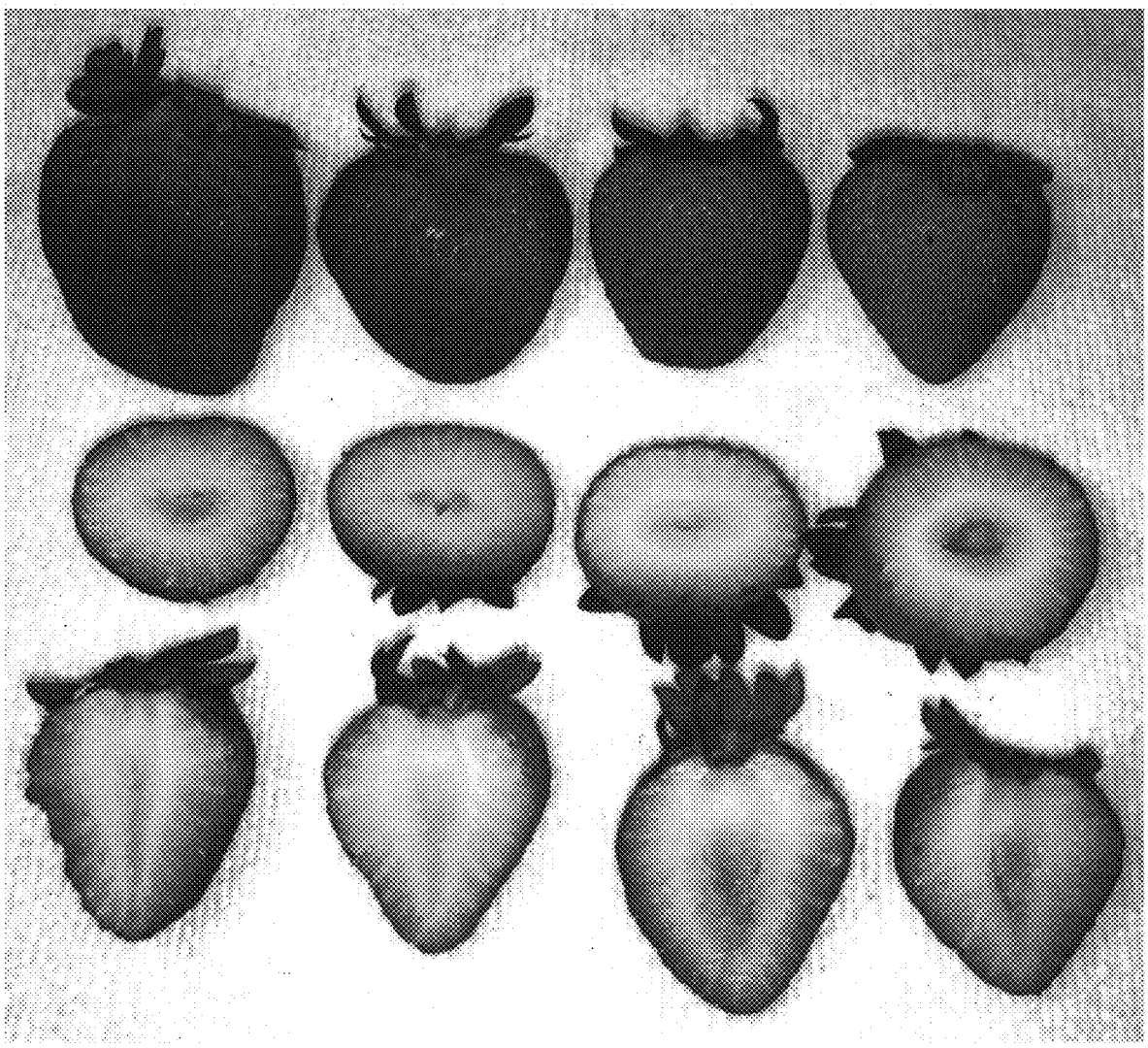
FIG. 4 shows typical internal and external mature fruit characteristics of 'SANTA MARIA', taken in the month of March 2020.

The new variety 'SANTA MARIA' has not been observed under all possible environmental conditions. The characteristics of the new variety 'SANTA MARIA' may vary in detail, depending upon variations in environmental factors, including weather (temperature, humidity and light intensity), day length, soil type and location. In addition, the characteristics of any parental variety or comparison variety included in Tables 1, 2 and 3 of the present invention may vary in detail, depending upon variations in environmental factors, including weather (temperature, humidity and light intensity), day length, soil type and location.

The aforementioned photographs, together with the following description of the new variety 'SANTA MARIA', unless otherwise noted, are based on observations taken during the 2019-2020 growing season in Hillsborough County, Fla. These measurements and ratings were taken from plants of 'SANTA MARIA' dug from a high-elevation nursery located in Siskiyou County, Calif. during mid-September 2019 and planted approximately four to five days later in Hillsborough County, Fla. The approximate age of the observed plants is five months. Yield observations including average weight and marketable yield, along with fruit quality characteristics including soluble solids, are averaged from four years of data collected from the 2015-2016 through 2018-2019 growing seasons. Flower measurements and characteristics are from secondary flowers unless otherwise noted. Fruit characteristics and measurements are from secondary fruit, unless otherwise noted.

Where noted, color terminology follows The Royal Horticultural Society Colour Chart, London (2007).

The following characteristics describe fruit, plant, stolon, foliage, fruiting truss, flower, reproductive organs and pest and disease characteristics of the new strawberry 'SANTA MARIA'.

Fruit characteristics:

*Color of mature fruit*.—RHS 46A (red).

*Color of internal flesh (excluding core)*.—RHS 46B (medium red).

*Color of core*.—RHS 46C (medium red).

*Average length (cm)*.—3.6.

*Average width (cm)*.—3.5.

*Size*.—Large.

*Average length/width ratio*.—1.04 (ranges from as long as broad to slightly longer than broad).

*Average calyx diameter (cm)*.—3.3.

*Season average weight (gm)*.—28.7.

*Achene color, shaded side*.—RHS 153B (yellow green group).

*Achene color, sun-exposed side*.—RHS 185A (greyed purple group).

*Average achene weight (mg)*.—0.6.

*Average achenes per berry*.—264.8.

*Average achene length (mm)*.—1.5.

*Average achene width (mm)*.—0.8.

*Season marketable yield (gm/plant)*.—387.

*Predominant shape*.—Cordate (cordiform).

*Difference in shape between primary and secondary fruit*.—Ranges from moderate to large.

*Band without achenes*.—Narrow.

*Evenness of surface*.—Ranges from slightly uneven to strongly uneven.

*Evenness of color*.—Even.

*Glossiness*.—Ranges from medium to strong.

*Insertion of achenes*.—Even to slightly below surface.
*Position of calyx attachment*.—Inserted.
*Attitude of sepals*.—Outward to slightly upward.
*Size of calyx in relation to fruit diameter*.—Slightly smaller.
*Adherence of calyx* (*when fully ripe*).—Strong.
*Firmness of flesh*.—Firm.
*Distribution of red color of the flesh*.—Marginal and central.
*Hollow center expression*.—Moderate.
*Cavity length* (*mm*)—0 to 25.
*Cavity width* (*mm*).—0 to 5.
*Flavor*.—Good.
*Soluble solids* (*% brix*).—7.0.
*Time of first flowering*.—Early (mid October in Hillsborough County, Fla.).
*Flowering season*.—October-February.
*Time of first fruit*.—Early (mid November in Hillsborough County, Fla.).
*Fruiting season*.—November-March.
*Harvest period*.—Mid-November to March (in Hillsborough County, Fla.).
*Post harvest fruit longevity*.—9-11 days if stored according to industry standards.
*Type of bearing*.—Not remontant.

Plant characteristics:
*Average height* (*cm*).—23.7.
*Average spread* (*cm*).—39.3.
*Size*.—Medium.
*Habit*.—Upright.
*Density*.—Medium.
*Vigor*.—Medium to high.

Stolon characteristics:
*Color*.—RHS 145A (yellow green group).
*Anthocyanin coloration*.—RHS 182A (greyed red group).
*Anthocyanin intensity*.—Ranges moderate to strong.
*Pubescence*.—Dense.
*Attitude of hairs*.—Slightly outward.
*Average quantity in nursery* (*per square foot*).—17 to 18 (high).
*Average diameter at the bract* (*mm*).—3.1 (medium).
*Length* (*cm*).—25 to 35.

Terminal leaflet characteristics:
*Average length* (*cm*).—7.4.
*Average width* (*cm*).—7.8.
*Average area terminal* ($cm^2$).—57.6.
*Average length/width ratio*.—0.96 (slightly more broad than long).
*Shape of base*.—Obtuse.
*Margins* (*shape of teeth*).—Obtuse (serrate to crenate).
*Average serrations per leaf*.—20.9.

Foliage characteristics:
*Color of upper surface*.—RHS 139A (green group).
*Color of underside*.—RHS 147B (green group).
*Number of leaflets*.—3.
*Leaf size*.—Medium.
*Average length* (*cm*).—10.8.
*Average width* (*cm*).—13.4.
*Average area foliage* ($cm^2$).—146.0.
*Shape in cross section*.—Slightly concave.
*Texture/interveinal blistering*.—Ranges from medium to strong.
*Leaf glossiness*.—Ranges from medium to strong.
*Leaf variegation*.—Absent.
*Venation pattern*.—Pinnate.
*Apex descriptor*.—Obtuse.

Petiole characteristics:
*Petiole color*.—RHS 145A (yellow green group).
*Average length* (*cm*).—16.4.
*Average diameter* (*mm*).—4.1.
*Petiolule color*.—RHS 145A (yellow green group).
*Petiolule average length* (*mm*).—15.6.
*Average petiolule diameter* (*mm*).—1.9.
*Attitude of hairs*.—Strongly outward.
*Texture*.—Moderate to smooth.
*Frequency of bract leaflets*.—None to many (75% occurrence).
*Size of bract leaflets*.—Small to large.
*Pubescence*.—Light to moderate.

Stipule characteristics:
*Color*.—RHS 157B (yellow green group).
*Anthocyanin coloration*.—RHS 60A (red group).
*Anthocyanin intensity*.—Weak.
*Average length* (*mm*).—34.53.
*Average width* (*mm*).—8.31.
*Base descriptor*.—Truncate.
*Apex descriptor*.—Obtuse.
*Shape*.—Triangular.
*Margin*.—Smooth.
*Texture*.—Moderate to smooth.

Fruiting truss characteristics:
*Anthocyanin coloration*.—RHS 182A (greyed red group).
*Anthocyanin intensity*.—Weak.
*Average length at maturity* (*cm*).—18.9.
*Position relative to foliage*.—Level with.
*Flower quantity* (*average per plant season long*).—35-45 (high).
*Fruits per truss*.—2 to 4.
*Pedicel attitude of hairs*.—Slightly outward.
*Pubescence*.—Strong.
*Attitude at first pick*.—Prostrate.
*Average pedicel length* (*cm*).—7.2.
*Average pedicel diameter* (*mm*).—2.1.
*Pedicel texture*.—Moderate to smooth.
*Pedicel color*.—RHS N144A (yellow green group).
*Average peduncle length* (*cm*).—3.5.
*Average peduncle diameter* (*mm*).—3.3.
*Peduncle texture*.—Moderate to smooth.
*Peduncle color*.—RHS N144A (yellow green group).

Flower characteristics:
*Flower bud shape*.—Pyriform.
*Average flower bud length* (*mm*).—21.1.
*Average flower bud diameter* (*mm*).—7.5.
*Flower bud color*.—RHS N144D (yellow green group).
*Flower depth* (*mm*).—16.4.
*Corolla* (*flower*) *average diameter* (*mm*).—27.2 (ranges from medium to large).
*Upper petal color*.—RHS 155C (white group).
*Lower petal color*.—RHS 155C (white group).
*Petal shape*.—Orbicular.
*Petal apex descriptor*.—Obtuse/rounded.
*Petal margin*.—Smooth.
*Petal base*.—Decurrent.
*Petal texture*.—Smooth.
*Petal average length* (*mm*).—10.3.
*Petal average width* (*mm*).—11.0.

*Petal average length/width ratio.*—0.94 (as long as broad).
*Average petals per flower.*—6.3.
*Upper sepal color.*—RHS 141B (green group).
*Lower sepal color.*—RHS N144D (yellow green group).
*Sepal shape.*—Cuneate.
*Sepal apex descriptor.*—Obtuse.
*Sepal margin.*—Serrate.
*Sepal texture.*—Moderately smooth.
*Sepal average length (mm).*—10.1.
*Sepal average width (mm).*—4.7.
*Sepal average length/width ratio.*—2.14.
*Average sepals per flower.*—12.2.
*Calyx average diameter (mm).*—28.0.
*Size of calyx relative to corolla.*—Slightly larger.
*Size of inner calyx relative to outer calyx.*—Same.
*Relative position of petals.*—Overlapping.

Reproductive organs:
*Receptacle color.*—RHS 147D (yellow green group).
*Pollen color.*—RHS 15A (yellow orange group).
*Stamen.*—Present.
*Average filament length (mm).*—2.3.
*Filament color.*—RHS 157B (green white group).
*Average anther length (mm).*—1.7.
*Anther shape.*—Ovoid.
*Anther color.*—RHS 16A (yellow orange color).
*Average pistils per flower.*—264.8.
*Pistil length (mm).*—0.5-1.5.
*Style length (mm).*—0-1.
*Style color.*—RHS 1A (green yellow group).
*Stigma diameter (mm).*—<0.1.
*Stigma shape.*—Simple.
*Ovary color.*—RHS 1D (green yellow group).
*Pollen amount.*—Abundant.

Disease and pest reactions:
*Powdery mildew (sphaerotheca macularis).*—Moderately susceptible.
*Angular leaf spot (xanthomonas fragariae).*—Moderately susceptible.
*Botrytis fruit rot (botrytis cinerea).*—Moderately susceptible.
*Fusarium wilt (fusarium oxysporum).*—Resistant.
*Anthracnose crown rot (colletotrichum fragariae).*—Moderately susceptible.
*Two-spotted spider mite (tetranychus urticae).*—Moderately susceptible.
*Winter hardiness.*—Moderate.

We claim:

1. A new and distinct strawberry plant named 'SANTA MARIA', as herein described and illustrated.

* * * * *